United States Patent [19]

Hales et al.

[11] Patent Number: 4,630,596

[45] Date of Patent: Dec. 23, 1986

[54] EMERGENCY CONTAINER FOR AN ACCIDENTALLY AMPUTATED MEMBER

[76] Inventors: Patrick Hales, 25 Allée de la Fontaine au Blanc, 78860 St Nom La Breteche; Jean-Pierre Laurier, Le Moulin de la Bonde, 78121 Crespieres; Gerard Pradet, 5 rue des Gate-Ceps, 92210 Saint-Cloud, all of France

[21] Appl. No.: 703,841

[22] Filed: Feb. 21, 1985

[30] Foreign Application Priority Data

Feb. 24, 1984 [FR] France ................... 84 02822
Nov. 13, 1984 [FR] France ................... 84 17309

[51] Int. Cl.[4] .................... A61F 7/10; A61F 17/00
[52] U.S. Cl. .................... 128/1 R; 128/399; 215/13 R
[58] Field of Search ............ 383/29; D3/30.1; 62/457, 371, 372; 128/1 R, 399, 1 B; 435/283, 1; D24/9; 215/11.3, 13 R, 12 A, 11 R; 206/229, 230

[56] References Cited

U.S. PATENT DOCUMENTS

| | | | |
|---|---|---|---|
| 2,598,532 | 8/1948 | Gibbon | 128/1 B |
| 2,862,307 | 8/1957 | Bloomer et al. | 312/1 |
| 3,664,535 | 5/1972 | Mette | 215/11 R |
| 3,931,886 | 1/1976 | Yamauchi | 215/11 R |
| 4,558,792 | 12/1985 | Cabernoch et al. | 215/11 R |

FOREIGN PATENT DOCUMENTS

142343  2/1976  United Kingdom ............ 215/13 R

*Primary Examiner*—Stephen C. Pellegrino
*Assistant Examiner*—John D. Ferros
*Attorney, Agent, or Firm*—Sughrue, Mion, Zinn, Macpeak and Seas

[57] ABSTRACT

An emergency container for an accidentally amputated member, the container comprising a rigid receptacle (1) having an insulating wall, an insulating cover (2) for closing the receptacle, the cover including an opening (3), a bag (5) made of flexible material and provided to be disposed inside the receptacle, with the opening of the bag coinciding with the opening (3) through the cover, and a stopper (4) for simultaneously closing the opening (3) and the bag (5).

12 Claims, 4 Drawing Figures

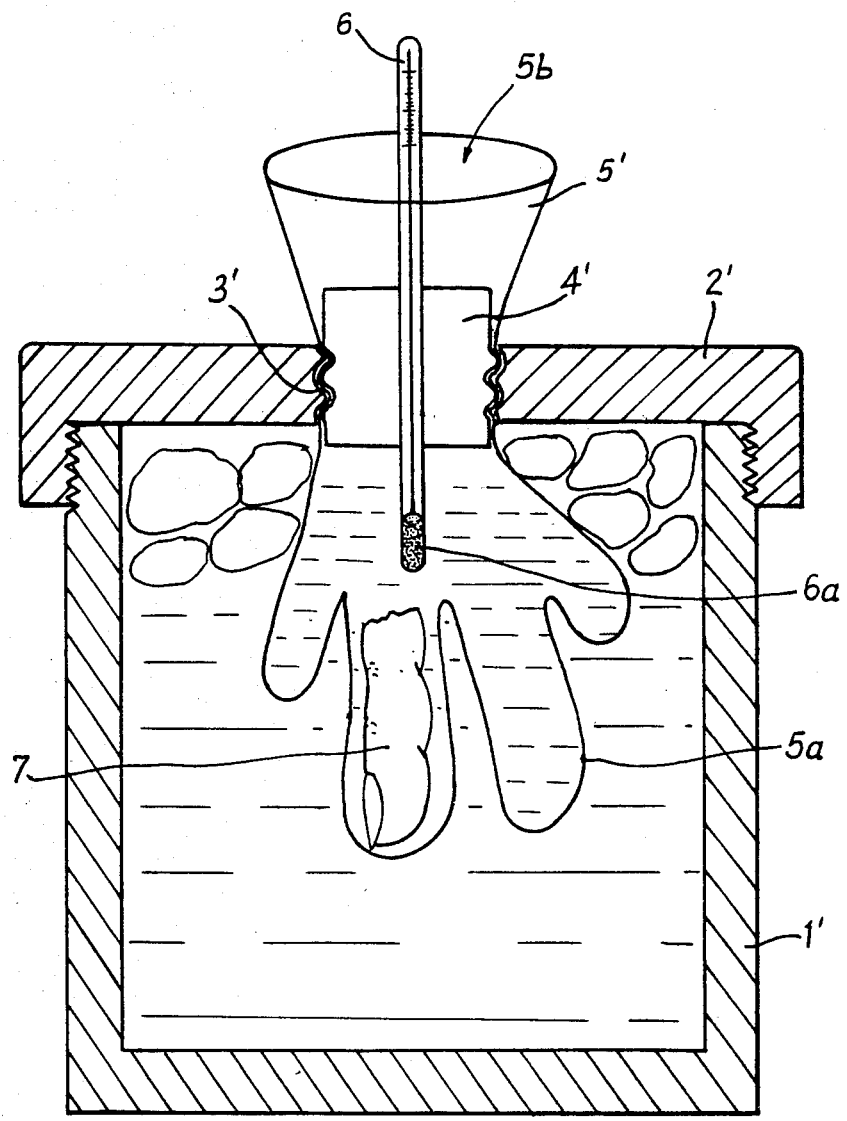

EMERGENCY CONTAINER FOR AN ACCIDENTALLY AMPUTATED MEMBER

The present invention relates to an emergency container for an accidentally amputated member, for conserving the member during transport to a center suitable for emergency reimplantation.

BACKGROUND OF THE INVENTION

Proper physiological conservation of an amputated member is essential if an attempt at reimplanting the member by micro-surgical techniques is to be successful.

At ambient temperature, the maximum waiting period is three hours.

If the member is cooled to a temperature in the range 2° C. to 4° C. at the moment of amputation, it may be conserved for as long as 36 hours.

It may still be conserved for as long as 22 hours after being exposed to ambient temperature prior to cooling for a period not exceeding two hours.

These periods apply to fragments of small size (fingers), they are considerably shortened (8 to 12 hours) once the volume is greater (limbs) or the fragment contains muscle, and also because it is more difficult to obtain uniform cooling. Excessive cooling below 0° C. gives rise to frost lesions and makes failure inevitable.

The first and most important problem, since success or failure depends upon it, is thus the problem of conserving the member as quickly as possible by cooling it, and transporting the member to a reimplantation center under proper temperature conditions.

The method currently used is to insert the fragment in a sealed plastic bag which is put on ice. This has several drawbacks as has been shown by various "SOS Hands" services:

the cooling is uneven;

the fragment may be damaged by direct mechanical contact; and some parts of the fragment may be frozen by direct contact with the ice or with icy water if the bag is not properly sealed, etc.

There is no way of knowing for sure during the operation whether one of these accidents has already occurred, and it is only after the operation has failed and it becomes apparent that is was useless or even damaging, that doubts arise. It is thus very much in the interest of the patient and of the surgeon to be sure prior to the operation that conservation has taken place under the best possible conditions.

Various scientific investigations have shown that for the best possible conservation:

the fragment must be inserted in a sealed bag;

the bag should be immersed in icy water rather than being put on ice in order to avoid partial freezing; and depending on the school of thought, either the fragment should be left dry, or else it should be wrapped in a cloth which is impregnated with Ringer's liquid or with physiological serum, or it should be directly immersed in said liquids.

This is very difficult to do in practice with means that are improvised on the spot, and the risks of error by omission or by over-enthusiastic commission are great.

Preferred embodiments of the present invention provide the patients and the first aid practitioner with simple, safe and quick conservation means.

SUMMARY OF THE INVENTION

According to the present invention, an emergency container for an accidentally amputated member comprises a rigid receptacle having an insulating wall, an insulating cover capable of sealing the container, and a bag of flexible material, the cover including an opening through which the opening to the bag is fitted, and a stopper for simultaneously closing the bag and the opening in the cover.

Preferably, the wall of the bag which is inserted through the opening in the cover and which lies between the cover and the stopper is itself constituted by a sealing gasket.

Preferably, the flexible bag is made of transparent material. Thus, by lifting the cover and hence lifting the bag together therewith, it is possible to observe the contents of the bag. It is also advantageous for the container to include a thermometer which should be placed so as to be readable from outside the container. The thermometer may be placed on a side wall of the container or it may pass through the cover or through the stopper into the flexible bag if the bag is filled with liquid.

Some schools of surgery prefer the member to be transported in a liquid medium (Ringer's liquid or physiological serum) while other schools prefer the member to be transported dry. In either case, it appears that the flexible bag containing the severed member (regardless of whether it includes liquid or not) is subjected during transport to damaging agitation, and usually rises to the surface of the water contained in the container. The severed member is thus at the same level as the ice, which is to be avoided both because of mechanical shocks and because of the temperature.

The present invention thus advantageously includes means for holdng the bottom of the flexible bag away from the cover and the stopper and close to the bottom of the container.

To make it easy to remove the flexible bag which in practice is fixed to the cover, it is preferable for the said means to be constituted by rigid members fixed to the cover.

An arc- or hoop-shaped member may be fixed to the cover, for example, and the bottom of the bag may be fixed thereto by any suitable means.

The inventors have also observed that to avoid, or at least to reduce, the movement of the water and the ice in the container, the container should be completely filled, at least at the moment of filling. If the container is filled before the bag is inserted therein, there is a danger of the container overflowing and also of water or ice entering the flexible bag.

It is thus advantageous to provide a second hole in the cover for topping up the container after the cover and its bag have been placed therein and after the bag has been closed by the stopper. If there is any overflow at this stage, the water does not penetrate into the bag since it is already closed by the stoppper.

BRIEF DESCRIPTION OF THE DRAWINGS

Embodiments of the invention are described by way of example with reference to the accompanying drawings, in which:

FIG. 4 is a section view through a second embodiment of a container in accordance with the invention.

MORE DETAILED DESCRIPTION

Figure 1:
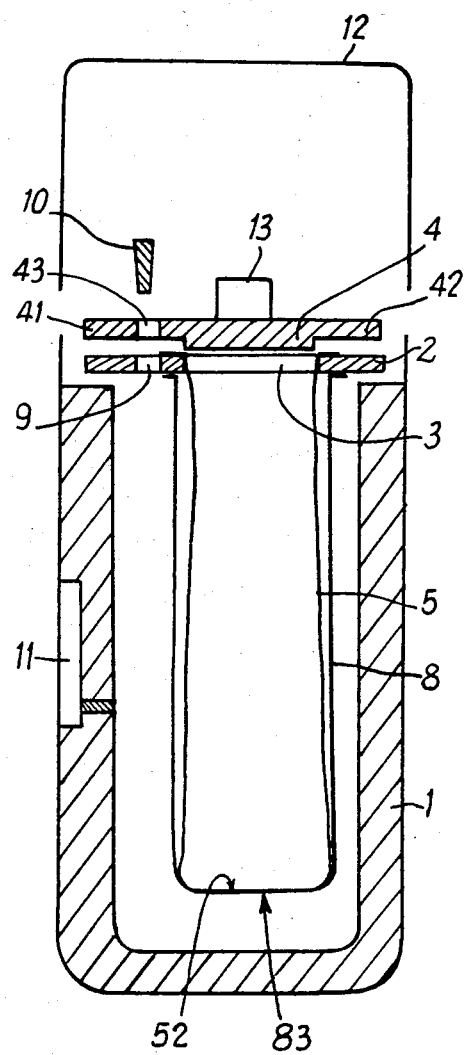
FIG. 1 is a diagrammatic section through an emergency container in accordance with the invention.
Figure 2:
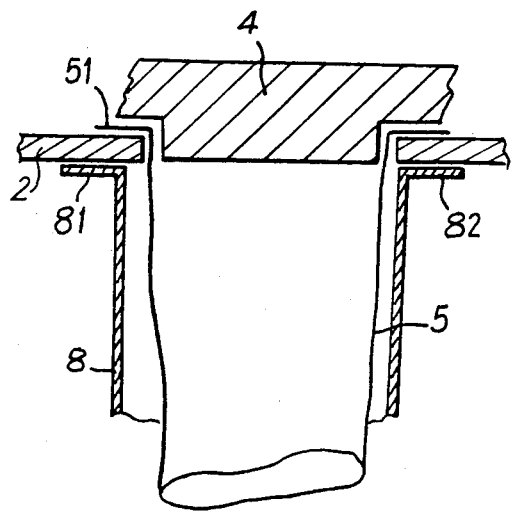
FIG. 2 is a section showing a detail of the FIG. 1 embodiment.
Figure 3:
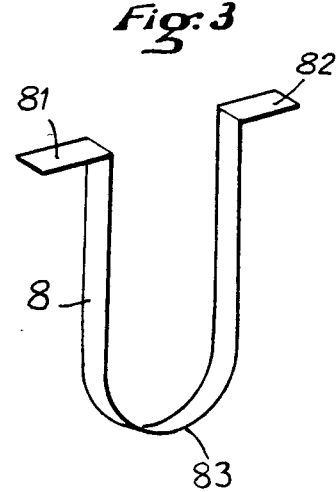
FIG. 3 is a perspective view one example of means for holding the bottom of the bag at the bottom of the container.

The receptacle 1 shown in FIG. 1 is in the shape of a rectangular box which is open at one end. Its walls are rigid and covered in thermally insulating material. A cover 2, which is also thermally insulating, is formed with a hole 3 and serves to close the receptacle 1. The hole 3 may be closed by a stopper 4. A flexible bag 5 is passed through the hole 3 between the cover 2 and the stopper 4. It may be passed freely through the hole 3 without being fixed thereto. In this manner it may easily be separated from the receptacle and its cover. However, this advantage is secondary relative to ensuring proper conservation conditions during transport. As shown in the section of FIG. 2, the rim 51 of the bag may be glued or welded to the rim of the hole 3 and/or to a surrounding margin. It could also be glued or welded to a margin around the hole 3 but on the inside face of the cover 2. However, it is highly advantageous to use the bag itself as a sealing gasket for the stoppper 4, in particular since it is the bag itself which needs to be closed in a sealed manner.

To prevent the bag from kinking or folding up, and thus rising to the top of the container (which is normally held with the cover on top), means are provided in accordance with the invention to hold the bottom of the bag at or near the bottom of the container. In the embodiment shown, these means comprise a hoop 8, wich may be made of rigid plastics material for example, having its ends 81 and 82 fixed to the cover 2 on either side of the hole 3. The bottom 52 of the bag 5 may be glued or welded to the curve constituting the end 83 of the hoop 8. Thus, when the cover 2 is placed on the receptacle 1 the bag 5 is properly positioned and is held in the proper position. If the container is not excessively shaken during transport, the temperature at the bottom of the container will be slightly greater than 0° C., which is advantageous for conservation of the organ being transported.

In order to facilitate complete filling of the container, a second hole 9 is provided in the cover 2. Thus, to fill the container, a certain quantity of water and ice is initially placed therein and then the cover 2 is put into place together with the bag 5. The hole 3 is then closed by means of the stopper 4. It is then possible to fill the container right up via the hole 9 until it overflows. Since the stoppper 4 closes the hole 3 there is no risk of water getting into the bag 5. The hole 9 is then clsoed by a stopper 10. In the embodiment shown, in FIG. 1 the stopper 4 includes fins 41 and 42 for hiding the cover 2, for example for reasons of appearance. In this case, a hole 43 is provided through the fin 41 in alignment with the hole 9 through the cover 2.

In a particular embodiment of the invention, a thermometer 11 is placed in the wall of the receptacle to give an outside indication of the the temperature inside the container. It is thus possible to read the temperature of the cooling water inside the container at any moment. If this temperature rises above a given value, for example if the water temperature rises above 4° C., the stopper 10 may be removed and a quantity of water poured out to leave room for more ice, and the container can then be topped up again with water.

The assembly may be covered by a cap 12 which is used, for example, to measure the initial quantity of water and/or ice to be inserted into the container. Instructions for use are advantageously written on a wall of the container.

A knob or handle 13 may be provided for manipulating the stopper.

In the embodiment shown in FIG. 4, the container in accordance with the invention comprises a receptacle 1' having a cover 2'. The receptacle and the cover are made of thermally insulating material and the cover serves to close the receptacle in a sealed and thermally isolating manner, e.g. by being screwed thereon and by means of a sealing ring or gasket. The cover could alternately be hinged to one side of the receptacle and be fitted with a suitable fastening. The receptacle may be cylindrical or it may have a square or polygonal section according to choice. The opening preferably occupies the entire cross-section of the receptacle as in the first example so as to make it easier to use, as described below.

According to an advantageous characteristic of the invention, the cover is provided with an opening 3', which is closed by a stopper 4', and the stopper is contained in a pocket formed by a bag 5' which thus has a closed portion 5a to be placed inside the receptacle while leaving the stopper free to be removed via the open portion 5b of the bag. In the example shown, the flexible bag is filled with liquid in which the severed member is immersed.

A thermometer 6 may pass through the stopper 4' so that its sensitive bulb 6a is inside the container. The thermometer thus indicates the temperature of the liquid in which the transported organ is immersed. Alternatively, the thermometer may pass through the cover or may be placed in the wall of the container.

In the example shown, the bag is shaped to house one or more fingers on an entire hand. It is advantageously in the shape of a glove. Models of various sizes may be provided on the same principle (e.g. for fingers, hands, feet, limbs).

To use the container in accordance with the invention, the severed member, e.g. a finger 7, is placed in the bag 5' which is then filled with a suitable liquid, e.g. physiological serum or Ringer's liquid. For this purpose, the container may be stored together with a dose of suitable liquid contained in a bottle or a plastic dispenser. The bag is placed through the opening 3' in the cover 2' and is then closed by the stopper 4'. The container can then be filled with water and ice. The liquid in the container then takes up a temperature of 0' C. and remains at that temperature until all the ice has melted. If the conservation is to continue for a long time, ice should be added as often as may be necessary. Provided the container is a good insulator, each ice refill should last for several hours. A refill is performed by unscrewing the cover from the receptacle. While this is going on, the fragment 7 may be observed in the bag, since the bag is advantageously made of transparent plastic.

Since the liquid in the container is at 0' C., there is no danger of the liquid in the bag freezing. The stopper 4' may be a less good insulator than the walls of the receptacle and of the cover so as to ensure that the temperature inside the bag is slightly greater than 0° C.

Finally, it is advantageous to print on the outside walls of the container:

instructions for use, including the expected time between refills;

precautions to be taken with the fragments;
instructions concerning the patient; and
the addresses of all the centers in, for example, the European Confederation of Emergency Centers for Severed Hands.

The container is thus a physiological icebox suitably arranged for transport and physiological conservation specific to fingers or other amputated members for the purpose of surgically reimplanting them at specialized centers and under the best possible conditions.

Such a container with a trasparent bag inside, and if so desired with a dose of Ringer's liquid, should be kept on site at places where accidents are likely to happen (factories, workshops, schools, the army . . . ). The container makes it possible to transport the severed fragment over long distances and over extended periods of time (30 to 37 hours) under the best possible conditions.

We claim:

1. A portable emergency container for conserving an accidentally amputated member, the container comprising: a rigid, open topped receptacle having thermally insulating walls and a thermally insulating base, said receptacle being adapted to hold iced water, a thermally insulating cover for closing the open top of the receptacle, said cover defining a through opening, a bag of flexible material adapted to carry an amputated member and be immersed in iced water inside the receptacle with an opening of the bag coinciding with the opening of the cover, and a stopper for simultaneously closing the openings in both the cover and the bag to thereby maintain an amputated member at a near freezing temperature to implement the prolonged conservation of said member.

2. An emergency container according to claim 1, wherein a body of the bag passes through the opening in the cover and bag material lines a wall of the opening through the cover and constitutes a sealing gasket therein.

3. An emergency container according to claim 1, wherein the flexible bag is made of transparent material.

4. An emergency container according to claim 1, further comprising means for keeping an end of the flexible bag remote from the stopper proximate a bottom of the container and away from the cover.

5. An emergency container according to claim 4, wherein said means comprises a hoop fixed to the cover.

6. An emergency container according to claim 5, wherein the end of the bag is fixed by gluing or welding to a lower end of the hoop.

7. An emergency container according to claim 1, further comprising a thermometer incorporated therein.

8. An emergency container according to claim 7, wherein the thermometer is placed in the stopper.

9. An emergency container according to claim 7, wherein the thermometer is incorporated in a wall of the receptacle to indicate the temperature inside the receptacle.

10. An emergency container according to claim 1, wherein the cover has two holes, a first hole for receiving the flexible bag, and a second hole for filling the receptacle with ice water.

11. An emergency container according to claim 1, wherein the flexible bag has a physiological shape such as that of a glove.

12. An emergency container according to claim 1, further including a quantity of liquid disposed in the bag suitable for conserving a severed member.

* * * * *